(12) United States Patent
Gruier

(10) Patent No.: US 8,277,521 B2
(45) Date of Patent: Oct. 2, 2012

(54) MIXTURE OF FURFURAL AND 5-(ALKOXYMETHYL)FURFURAL DERIVATIVES FROM SUGARS AND ALCOHOLS

(75) Inventor: Gerardus Johannes Maria Gruier, Heemstede (NL)

(73) Assignee: Furanix Technologies B.V., Amsterdam (NL)

( * ) Notice: Subject to any disclaimer, the term of this patent is extended or adjusted under 35 U.S.C. 154(b) by 405 days.

(21) Appl. No.: 12/446,489

(22) PCT Filed: Sep. 5, 2008

(86) PCT No.: PCT/EP2008/007428
§ 371 (c)(1),
(2), (4) Date: Aug. 6, 2009

(87) PCT Pub. No.: WO2009/030511
PCT Pub. Date: Mar. 12, 2009

(65) Prior Publication Data
US 2010/0083565 A1    Apr. 8, 2010

(30) Foreign Application Priority Data
Sep. 7, 2007 (EP) .................................. 07017572

(51) Int. Cl.
*C10L 1/185* (2006.01)
*C07D 307/42* (2006.01)
(52) U.S. Cl. ........................... 44/350; 549/497; 549/502
(58) Field of Classification Search .................. 44/388, 44/350, 352; 585/251; 549/490, 503
See application file for complete search history.

(56) References Cited

U.S. PATENT DOCUMENTS

| | | | |
|---|---|---|---|
| 4,977,283 A | 12/1990 | Leupold et al. | |
| 7,520,905 B1 * | 4/2009 | Lightner | 44/388 |
| 2005/0112739 A1 * | 5/2005 | Golubkov | 435/161 |
| 2008/0033188 A1 * | 2/2008 | Dumesic et al. | 549/505 |
| 2009/0124839 A1 * | 5/2009 | Dumesic et al. | 585/251 |

FOREIGN PATENT DOCUMENTS

| | | |
|---|---|---|
| DE | 635783 C | 9/1936 |
| DE | 3621517 A1 | 1/1988 |
| EP | 0 356 703 A2 | 3/1990 |
| EP | 0 641 854 A1 | 3/1995 |
| EP | 1 834 950 A1 | 9/2007 |
| FR | 2 669 634 A1 | 5/1992 |
| RU | 2 203 279 C1 | 4/2003 |
| WO | 99/67409 A1 | 12/1999 |
| WO | 2006/063220 A2 | 6/2006 |
| WO | 2007/104514 A2 | 9/2007 |

OTHER PUBLICATIONS

K. Garves, "Acid catalyzed degradation of cellulose in alcohols", Journal of Wood Chemistry and Technology, vol. 8, No. 1, p. 121-134, 1988.
Tarabanko, V.E., et al., "Catalyzed carbohydrate dehydration in the presence of butanol at moderate temperatures", 2002. XP002385431 Abstract.
"Method of synthesis of 5-hydroxymethylfurfurol ethers uses sucrose or fructose as starting reactant", 2003. XP002385647 Abstract.
Lichtenthaler, F.W., et al., "Sugar-derived building blocks Part 26; Hydrophilic pyrroles, pyridazines and diazepinones from D-fructose and isomaltulose", Royal Society of Chemistry, vol. 3, No. 5, p. 201-209, 2001.
Chapter 15 of Advanced Organic Chemistry, by Jerry March, and in particular under reaction 5-4. (3rd ed., © 1985 by John Wiley & Sons, pp. 684-685).
Dumesi, James A et al. "Phase Modifiers Promote Efficient Production of Hydroxymethylfurfural from Fructose," Science vol. 312, No. 5782 (Jun. 30, 2006) pp. 1933-1937.
Lewkowski, Jaroslaw. "Synthesis, Chemistry and Applications of 5-Hydroxymethyl-furfural and Its Derivatives," ARKIVOC (2001) pp. 17-54.
Moreau et al., "Dehydration of fructose and sucrose into 5-hydroxymethylfurfural in the presence of 1-H-3 methyl imidazolium chloride acting both as solvent and catalyst," Journal of Molecular Catalysis A: Chemical 253 (2006) pp. 165-169.
UOP report Oppurtunities for Biorenewables in Oil Refineries Final Technical Report, Submitted to: U.S. Department of Energy (DOE Award Number:DE-FG36-05G015085), Published: Dec. 12, 2005.
Tashiro et al. "A New Strategy for the Preparation of Terephthalic Acid by the Aerobic Oxidation of p-Xylene Using N-Hydroxyphthalimide as a Catalyst," Adv. Synth. Catal. vol. 343, No. 2, (2001) pp. 220-225.

* cited by examiner

*Primary Examiner* — Ellen McAvoy
*Assistant Examiner* — Latosha Hines
(74) *Attorney, Agent, or Firm* — Hoffmann & Baron, LLP

(57) ABSTRACT

Accordingly, the current invention provides a method for the manufacture of a mixture of a furfural and a 5-(alkoxymethyl) furfural derivative by reacting a C5 and C6 sugar-containing starting material with an alcohol in the presence of an acid catalyst, followed by the hydrogenation and/or etherification of the mixture of furfural and 5-(alkoxymethyl)furfural to convert the aldehyde function of both 5-(alkoxymethyl)furfural and furfural into an alkoxymethyl function or methyl function.

15 Claims, No Drawings

MIXTURE OF FURFURAL AND 5-(ALKOXYMETHYL)FURFURAL DERIVATIVES FROM SUGARS AND ALCOHOLS

CROSS-REFERENCE TO RELATED APPLICATIONS

This application is the National Stage of International Application No. PCT/EP2008/007428, filed Sep. 5, 2008, which claims the benefit of European Application No. 07017572.4, filed Sep. 7, 2007, the contents of which is incorporated by reference herein.

TECHNICAL FIELD

The present invention concerns a method for the manufacture of a mixture of furfural and 5-(alkoxymethyl)furfural (RMF) derivatives from a mixed feed containing both pentoses (C5 sugars) and hexoses (C6 sugars).

BACKGROUND ART

From DE635783 the preparation of alkoxymethylfurfurals and levulinic acid alkyl esters is known, using glucose or a glucose-containing starting material. For instance, saccharose, a disaccharide of glucose end fructose (both C6 sugars) has been used. The reactions provide primarily levulinic acid derivatives.

Fuel, fuel additives and various chemicals used in the petrochemical industry are derived from oil, gas and coal, all finite sources. Biomass, on the other hand, is considered a renewable source. Biomass is biological material (including biodegradable wastes) which can be used for the production of fuels or for industrial production of e.g. fibres, chemicals or heat. It excludes organic material which has been transformed by geological processes into substances such as coal or petroleum.

Production of biomass derived products for non-food applications is a growing industry. Bio-based fuels are an example of an application with strong growing interest.

Biomass contains sugars (hexoses and pentoses) that may be converted into value added products. Current biofuel activities from sugars are mainly directed towards the fermentation of sucrose or glucose into ethanol or via complete breakdown via Syngas to synthetic liquid fuels. EP 0641 854 describes the use of fuel compositions comprising of hydrocarbons and/or vegetable oil derivatives containing at least one glycerol ether to reduce particulate matter emissions.

More recently, the acid catalysed reaction of fructose has been re-visited, creating HMF as an intermediate of great interest. Most processes investigated have the disadvantage that HMF is not very stable at the reaction conditions required for its formation. Fast removal from the water-phase containing the sugar starting material and the acid catalyst has been viewed as a solution for this problem. Researchers at the University of Wisconsin-Madison have developed a process to make HMF from fructose. HMF can be converted into monomers for plastics, petroleum or fuel extenders, or even into fuel itself. The process by prof. James Dumesic and co-workers first dehydrates the fructose in an aqueous phase with the use of an acid catalyst (hydrochloric acid or an acidic ion-exchange resin). Salt is added to salt-out the HMF into the extracting phase. The extracting phase uses an inert organic solvent that favors extraction of HMF from the aqueous phase. The two-phase process operates at high fructose concentrations (10 to 50 wt %), achieves high yields (80% HMF selectivity at 90% fructose conversion), and delivers HMF in a separation-friendly solvent (DUMESIC, James A, et al. "Phase modifiers promote efficient production of Hydroxymethylfurfural from fructose". Science. 30 juni 2006, vol. 312, no. 5782, p. 1933-1937). Although the HMF yields from this process are interesting, the multi-solvent process has cost-disadvantages due to the relatively complex plant design and because of the less than ideal yields when cheaper and less reactive hexoses than fructose, such as glucose or sucrose, are used as a starting material. HMF is a solid at room temperature which has to be converted in subsequent steps to useful products. Dumesic has reported an integrated hydrogenolysis process step to convert HMF into dimethylfuran (DMF), which is assumed to be an interesting gasoline additive.

In WO 2006/063220 a method is provided for converting fructose into 5-ethoxymethylfurfural (EMF) at 60° C., using an acid catalyst either in batch during 24 hours or continuously via column elution during 17 hours. Applications of EMF were not discussed.

Also in copending patent application PCT/EP2007/002145 the manufacture of HMF ethers are described, including the use of such ethers as fuel or fuel additive. Indeed, both the methyl ether and the ethyl ether (methoxymethylfurfural, or MMF; ethoxyethylfurfural or EMF) were prepared and tested. The invention of the copending patent application, however, was limited to the use of hexose feedstock with preferably primary C1-C5 alcohols. Use of hexose and pentose mixed feed with secondary and tertiary alcohols was not considered, whereas the only example of a branched primary alcohol was considered. Although 5-alkoxymethylfurfural derivatives are useful as fuel or fuel additive, the inventors found that the ethers leave room for improvement, in particular when used in higher concentration blends with fuels such as gasoline, kerosene, diesel, biodiesel or green diesel. The inventors have developed further derivatization routes addressing the negative effect of the aldehyde functionality of furfural and its derivatives on the fuel blend properties, allowing now also to start with a mixed pentose/hexose feed as the poorly fuel-soluble furfural that is obtained from pentoses will now concurrently be converted to better soluble furfuryl ethers or methylfuran during aldehyde to alcohol hydrogenation/etherification or aldehyde to $CH_3$ hydrogenation, respectively. Therefore the removal of the pentoses from the mixed pentose/hexose biomass feed is no longer required.

Surprisingly, the inventors have found that a combination of a derivative from 5-alkoxymethylfurfural and a derivative of furfural, preferably the corresponding furfural derivative, have superior blending properties compared to the 5-alkoxymethylfurfural alone or the blend of 5-alkoxymethylfurfural with furfural.

DISCLOSURE OF INVENTION

Accordingly, the current invention provides a method for the manufacture of a mixture of a furfural and a 5-(alkoxymethyl)furfural derivative by reacting a C5 and C6 sugar-containing starting material with an alcohol in the presence of an acid catalyst, followed by the hydrogenation and/or etherification of the mixture of furfural and 5-(alkoxymethyl)furfural to convert the aldehyde function of both 5-(alkoxymethyl)furfural and furfural into an alkoxymethyl function or a methyl function.

When the reaction product of the above method is used as a starting material for a subsequent conversion to a fuel, a fuel additive or as a fuel or a fuel additive intermediate, the reaction product does not necessarily need to be pure. Indeed, in the preparation of fuel and fuel additives from biomass, the reaction product may contain non-interfering components such as levulinic acid derivatives and the like. For ease of reference, however, the method and the reaction product are described in terms of the reaction of a mixed pentose/hexose-containing starting material, resulting in a mixture of furfural and 5-(alkoxymethyl)furfural. The current invention also provides for the use of the reaction product made according to the present invention as fuel or as fuel additive. Fuels for blending with the product of the present invention include but are not limited to gasoline and gasoline-ethanol blends, kerosene, diesel, biodiesel (refers to a non-petroleum-based diesel fuel consisting of short chain alkyl (methyl or ethyl) esters, made by transesterification of vegetable oil, which can be used (alone, or blended with conventional petrodiesel), Fischer-Tropsch liquids (for example obtained from GTL, CTL or BTL gas-to-liquids/coal-to-liquids/biomass to liquids processes), diesel-biodiesel blends and green diesel and blends of diesel and/or biodiesel with green diesel (green diesel is a hydrocarbon obtained by hydrotreating biomass derived oils, fats, greases or pyrolysis oil; see for example the UOP report OPPORTUNITIES FOR BIORENEWABLES IN OIL REFINERIES FINAL TECHNICAL REPORT, SUBMITTED TO: U.S. DEPARTMENT OF ENERGY (DOE Award Number: DE-FG36-05GO15085). The product is a premium diesel fuel containing no sulfur and having a cetane number of 90 to 100). Fuels for blending with the product of the present invention may also include one or more other furanics, wherein the expression furanics is used to include all derivatives of furan and tetrahydrofuran. The invention also provides a fuel composition comprising a fuel element as described above and the reaction product made according to the present invention.

MODE(S) FOR CARRYING OUT THE INVENTION

Biomass resources are well known. The components of interest in biomass are those feeds that can release a mixture of hexoses and at least 5% of pentoses (hereinafter referred to as mixed pentose and hexose-containing starting material. In organic chemistry, a hexose is a monosaccharide with six carbon atoms having the chemical formula $C_6H_{12}O_6$. Hexoses are classified by functional group, with aldohexoses having an aldehyde at position 1, and ketohexoses having a ketone at position. Suitable 6-carbon monosaccharides include but are not limited to fructose, glucose, galactose, mannose, and their oxidized, reduced, etherified, esterified and amidated derivatives, e.g. aldonic acid or alditol, with glucose being the most abundant, the most economic and therefore the most preferred monosaccharide albeit less reactive than fructose. A pentose is a monosaccharide with five carbon atoms, having the chemical formula $C_5H_{10}O_5$. They either have an aldehyde functional group in position 1 (aldopentoses), or a ketone functional group in position 2 (ketopentoses). Suitable 5-carbon monosaccharides include but are not limited to Arabinose, Ribose, Ribulose, Xylose, Xylulose, Lyxose and their oxidized, reduced, etherified, esterified and amidated derivatives.

On the other hand, the current inventors have also succeeded to convert sucrose, which is also available in great abundance. Other disaccharides that may be used include maltose, cellobiose and lactose. The polysaccharides that may be used include cellulose, inulin (a polyfructan), starch (a polyglucan) and hemi-cellulose. The polysaccharides and disaccharides are converted into their monosaccharide component(s) and dehydrated during the manufacture of the 5-HMF ether.

The alcohol used in the method of the current invention preferably bears a single hydroxyl group, which may be in a primary, secondary or even tertiary position. The alcohol may comprise from 1 to 20 carbon atoms, preferably from 1 to 8 carbon atoms, whereby the alcohols with 4 or more carbon atoms preferably have a branched carbon backbone.

Preferred alcohols used in the method of the current invention include methanol, ethanol, 1-propanol, 2-propanol, isobutanol, tert-butanol, isoamyl alcohol, isooctyl alcohol. Also blends of alcohols may be used, e.g., of isobutanol and tert-butanol.

The amount of alcohol used during the manufacture of the HMF ether of the present invention is preferably at least equimolar on the hexose content of the feedstock, but typically is used in much greater excess. Indeed, the alcohol (such as tert-butanol) may be used as solvent or co-solvent. In such a case, a sufficient amount of alcohol is present to form the HMF ether.

The acid catalyst in the method of the present invention can be selected from amongst (halogenated) organic acids, inorganic acids, Lewis acids, ion exchange resins and zeolites or combinations and/or mixtures thereof. It may be a homogeneous catalyst, but heterogeneous catalysts (meaning solid catalysts) are preferred for purification reasons. The HMF ether can be produced with a protonic, Brønsted or, alternatively, a Lewis acid or with catalysts that have more than one of these acidic functionalities.

The protonic acid may be organic or inorganic. For instance, the organic acid can be selected from amongst oxalic acid, levulinic acid, maleic acid, trifluoro acetic acid (triflic acid), methansulphonic acid or para-toluenesulphonic acid. Alternatively, the inorganic acid can be selected from amongst (poly)phosphoric acid, sulphuric acid, hydrochloric acid, hydrobromic acid, nitric acid, hydroiodic acid, optionally generated in situ.

Certain salts may be used as catalyst, wherein the salt can be any one or more of $(NH_4)_2SO_4/SO_3$, ammonium phosphate, pyridinium chloride, triethylamine phosphate, pyridinium salts, pyridinium phosphate, pyridinium hydrochloride/hydrobromide/perbromate, DMAP, aluminium salts, Th and Zr ions, zirconium phosphate, Sc and lanthanide ions such as Sm and Y as their acetate or trifluoroactate (triflate) salt, Cr-, Al-, Ti-, Ca-, In-ions, $ZrOCl_2$, $VO(SO_4)_2$, $TiO_2$, V-porphyrine, Zr-, Cr-, Ti-porphyrine.

Lewis acids selected as dehydration catalyst can be any one of $ZnCl_2$, $AlCl_3$, $BF_3$.

Ion exchange resins can be suitable dehydration catalysts. Examples include Amberlite™ and Amberlyst™, Diaion™ and Levatit™. Other solid catalyst that may be used include natural clay minerals, zeolites, supported acids such as silica impregnated with mineral acids, heat treated charcoal, metal oxides, metal sulfides, metal salts and mixed oxides and mixtures thereof. If elevated reactions temperatures are used, as defined hereafter, then the catalyst should be stable at these temperatures.

An overview of catalysts that may be used in the method of the current invention may be found in Table 1 of the review article prepared by Mr. Lewkowski: "Synthesis, chemistry and applications of 5-hydroxymethylfurfural and its derivatives" Arkivoc. 2001, p. 17-54. The amount of catalyst may vary, depending on the selection of catalyst or catalyst mixture. For instance, the catalyst can be added to the reaction mixture in an amount varying from 0.01 to 40 mole % drawn on the hexose content of the feed, preferably from 0.1 to 30 mole 10%, more preferably from 1 to 20 mole %.

In the preferred embodiment, the catalyst is a heterogeneous catalyst.

The temperature at which the reaction is performed may vary, but in general it is preferred that the reaction is carried out at a temperature from 50 to 300 degrees Celsius, preferably from 125 to 250 degrees Celsius, more preferably from 150 to 225 degrees Celsius. In general, temperatures higher than 300 are less preferred as the selectivity of the reaction reduces and as many by-products occur, inter alia caramelisation of the sugar. Performing the reaction below the lowest temperature is also less preferable because of the low reaction rate. If the reactions are carried out above the boiling temperature of water, then the reactions are preferably carried out under pressure, e.g., 10 bar nitrogen or higher.

The mixed pentose/hexose starting material is typically dissolved or suspended in a solvent, which can also be the alcohol reactant, in order to facilitate the reaction. The solvent system may be one or more selected from the group consisting of water, sulfoxides, preferably DMSO, ketones, preferably methyl ethylketone, methylisobutylketone and acetone, ethylene glycol ethers, preferably diethyleneglycol dimethyl ether (diglyme) or the reactant alcohol. Also so-called ionic liquids may be used. The latter refers to a class of inert ionic compounds with a low melting point, which may therefore be used as solvent. Examples thereof include e.g., 1-H-3-methyl imidazolium chloride, discussed in "Dehydration of fructose and sucrose into 5-hydroxymethylfurfural in the presence of 1-H-3-methyl imidazolium chloride acting both as solvent and catalyst", by Claude Moreau et al, Journal of Molecular Catalysis A: Chemical 253 (2006) 165-169.

The amount of solvent is preferably present in sufficient amounts to dissolve or suspend the starting material and enough to limit undesired side-reactions.

The method of the current invention may be carried out in a batch process or in a continuous process, with or without recycle of (part of) the product stream to control the reaction temperature (recycle via a heat exchanger). For instance, the method of the invention can be performed in a continuous flow process. In such method, homogenous catalysts may be used and the residence time of the reactants in the flow process is between 0.1 second and 10 hours, preferably from 1 second to 1 hours, more preferably from 5 seconds to 20 minutes.

Alternatively, the continuous flow process may be a fixed bed continuous flow process or a reactive (catalytic) distillation process with a heterogeneous acid catalyst. To initiate or regenerate the heterogeneous acid catalyst or to improve performance, an inorganic or organic acid may be added to the feed of the fixed bed or reactive distillation continuous flow process. In a fixed bed process, the liquid hourly space velocity (LHSV) can be from 1 to 1000, preferably from 5 to 500, more preferably from 10 to 250 and most preferably from 25 to 100 $min^{-1}$.

The above process results in a mixture of a stable HMF ether with furfural, which mixture can then be converted into a further derivative before being used as fuel and/or as fuel additive.

The invention further concerns the use of the mixture of 5-(alkoxymethyl)furfural and furfural in a hydrogenation/etherification process to convert the aldehyde function of both 5-(alkoxymethyl)furfural and furfural into an alkoxymethyl function to use the resulting product as a fuel or fuel component. The invention further concerns the use of the mixture of 5-(alkoxymethyl)furfural and furfural in a hydrogenation process to convert the aldehyde function of, preferably, both 5-(alkoxymethyl)furfural and furfural into a $CH_3$ function to use as a fuel and/or fuel component. Of particular interest is the use of the ethers in diesel, biodiesel or "green diesel", given its (much) greater solubility therein than ethanol. Conventional additives and blending agents for diesel fuel may be present in the fuel compositions of this invention in addition to the above mentioned fuel components. For example, the fuels of this invention may contain conventional quantities of conventional additives such as cetane improvers, friction modifiers, detergents, antioxidants and heat stabilizers, for example. Especially preferred diesel fuel formulations of the invention comprise diesel fuel hydrocarbons and HMF ether as above described together with peroxidic or nitrate cetane improvers such as ditertiary butyl peroxide, amyl nitrate and ethyl hexyl nitrate for example.

The addition of the ethers of the invention to diesel fuel results in similar $NO_x$ numbers and a slight increase in CO emissions; however, the addition of sufficient amounts of cetane improvers can be utilized to reduce the $NO_x$ and CO emissions well below the base reference fuel.

Examples are enclosed to illustrate the method of the current invention and the suitability of the products prepared therefrom as fuel. The examples are not meant to limit the scope of the invention.

The following abbreviations are used:
F=Furfural
HMF=5-(hydroxymethyl)furfural
MMF=5-(methoxymethyl)furfural
EMF=5-(ethoxymethyl)furfural
nBuMF=5-n(butoxymethyl)furfural
FME=Furfuryl methyl ether
FEE=Furfuryl ethyl ether
DMMF=di(methoxymethyl)furan
DEMF=di(ethoxymethyl)furan The substrate conversions and the selectivities and yields were calculated according to the formulas:
Conversion=100*[$n_0$(substrate)−$n_t$(substrate)]/$n_0$ substrate
Selectivity=100*$n_t$(product)/[$n_0$(substrate)−$n_t$(substrate)]
Yield=100*$n_t$(product)/$n_0$ substrate,
Where:
$n_0$—the initial number of moles
$n_t$—the number the moles of a compound at time "t".

Example 1

In a typical experiment, 32.5 mg of xylose, 32.5 mg glucose or fructose and 0.8 ml of ethanol were added in a reactor coated inside with Teflon. The mixture reacted under nitrogen (12.5 bar) in the presence of a solid acid catalyst (6.5 mg) for 1 h at 150° C. The three main peaks observed in the UV spectrum were identified as Furfural (F), 5-(hydroxymethyl) furfural (HMF) and 5-(ethoxymethyl)furfural EMF.

TABLE 1

| Xylose and | Catalyst | Y F (%) | Y HMF (%) | Y EMF (%) |
|---|---|---|---|---|
| Glucose | $CrCl_2$ | 23.2 | 4.8 | 11.5 |
| Glucose | Zeolite HY 5 | 7.9 | 2.1 | 5.7 |
| Glucose | Al(III) triflate | 24.6 | 0.3 | 4.3 |
| Fructose | $CrCl_2$ | 20.7 | 5.7 | 14.8 |
| Fructose | Zeolite HY 5 | 8.0 | 4.2 | 14.6 |
| Fructose | Al(III) triflate | 20.6 | 0.0 | 0.4 |

Example 2

In a typical experiment, 32.5 mg of xylose, 32.5 mg glucose or fructose and 0.8 ml of methanol were added in a reactor coated inside with Teflon. The mixture reacted under nitrogen (12.5 bar) in the presence of a solid acid catalyst (6.5 mg) for 1 h at 150° C. The three main peaks observed in the UV spectrum were identified as furfural (F), 5-(hydroxymethyl)furfural (HMF) and 5-(methoxymethyl)furfural (MMF).

TABLE 2

| Xylose and | Catalyst | Y F (%) | Y HMF (%) | Y MMF (%) |
|---|---|---|---|---|
| Glucose | CrCl$_2$ | 11.0 | 0.9 | 11.3 |
| Glucose | Al(III) triflate | 17.8 | 0.1 | 2.1 |
| Fructose | CrCl$_2$ | 9.6 | 2.2 | 18.9 |
| Fructose | Al(III) triflate | 18.4 | 0.0 | 1.5 |
| Fructose | Montmorillonite K 5 | 4.0 | 1.0 | 8.1 |

Example 3

In a typical experiment, 65 mg of a mixture of xylose, glucose and fructose (1:1:1, mass ratios) and 6.5 mg of a solid acid catalyst were mixed in a reactor coated inside with Teflon. 0.8 ml of an alcohol mixture (Methanol, Ethanol and n-Butanol with 1/2/1 volume ratio) was added and pressurized at 12.5 bar with nitrogen. The mixture reacted under for 1 h at 150° C. The main peaks observed in the UV spectrum were identified as F, HMF, EMF, MMF and nBuMF.

TABLE 3

| Catalyst | Y F (%) | Y HMF (%) | Y EMF (%) | Y MMF (%) | Y nBuMF (%) |
|---|---|---|---|---|---|
| CrCl$_2$ | 11.8 | 6.9 | 7.5 | 7.6 | 2.6 |
| Zeolite HY 5 | 5.1 | 5.4 | 4.2 | 5.1 | 0.8 |
| Zeolite HY 15 | 5.6 | 1.6 | 5.3 | 5.2 | 1.5 |
| Montmorillonite K 5 | 5.3 | 1.3 | 6.2 | 6.1 | 2.0 |
| Montmorillonite K 10 | 4.4 | 1.9 | 5.1 | 5.0 | 1.6 |
| Amberlyst36Wet | 3.3 | 2.1 | 6.2 | 6.4 | 1.7 |
| Zeoliteβ | 9.8 | 0.3 | 5.5 | 5.3 | 1.9 |

Example 4

Phase separation/crystallization temperature (° C.) of different Furanics/diesel mixtures.

The synthesized furanic compounds and their mixtures have been blended with regular diesel fuel at 1:1 ratio by volume. The miscibility of the blends was assessed in a Crystal 16™, a multiple reactor system developed by Avantium Technologies, Amsterdam. Therefore, the samples were cooled at a rate of 0.375° C./min, under continuous stirring at 700 rpm with a magnetic stir bar. Phase separation and/or crystallization was recorded by turbidity measurements. Furfural (F) and ethoxymethylfurfural (EMF) were not miscible with diesel at 1/1 ratio. DMMF is completely miscible at room temperature below 40% addition. Compared to diethers alone the presence of C-5 related monoethers improves the miscibility, especially when methanol is used as etherification agent.

TABLE 4

The miscibility of different furanics with regular diesel

| | Fuel composition | Component ratio v/v | Phase separation/ crystallization temperature (° C.) |
|---|---|---|---|
| 1 | Diesel | | −12 |
| 2 | Diesel + DMMF | 1:1 | >25 |
| 3 | Diesel + FME | 1:1 | −7 |
| 4 | Diesel + DMMF + FME | 2:1:1 | 14 |
| 5 | Diesel + DEMF | 1:1 | −8 |
| 6 | Diesel + FEE | 1:1 | −11 |

TABLE 4-continued

The miscibility of different furanics with regular diesel

| | Fuel composition | Component ratio v/v | Phase separation/ crystallization temperature (° C.) |
|---|---|---|---|
| 7 | Diesel + DEMF + FEE | 2:1:1 | −11 |
| 8 | Diesel + EMF | 1:1 | >25 |
| 9 | Diesel + F | 1:1 | >25 |
| 10 | Diesel + EMF + F | 2:1:1 | >25 |

Example 5

Emission Engine Testing with Diesel, FEE and DEMF

In a D9B diesel engine of a Citroen Berlingo test car, comparative testing was performed with normal commercial diesel fuel (experiment 1) and the same commercial diesel to which 25 vol. % FEE (experiment 2) or 25 vol % DEMF (experiment 3) was added, respectively. FEE and DEMF were added as a liquid and do not yield any mixing or flocculation problems at the blend ratio's used. The engine was run stationary with regular diesel initially, after which the fuel supply is switched to the 25 vol % FEE-diesel blend and the 25 vol % DEMF-diesel blend, respectively.

During stationary operation with the commercial diesel fuel and with the 25 vol % FEE and 25% DEMF blend, the following measurements were made: total particulate matter, volume, $O_2$, CO, $CO_2$, $NO_x$($NO+NO_2$) and total hydrocarbons.

Total particulate matter was sampled according to NEN-EN 13284-1

Particle size distribution was sampled according to VDI 2066-5

Volume was measured according to ISO 10780

Gases were sampled according to ISO 10396

$O_2$, CO and $CO_2$ were analysed according to NEN-ISO 12039

$NO_x$($NO+NO_2$) was analysed according to NEN-ISO 10849

Total hydrocarbons were analysed according to NEN-EN 13526.

TABLE 5

Gas analysis results of 100% commercial diesel fuel.

| Experiment | Component | Average Concentration | Emission |
|---|---|---|---|
| 1 | CO | 240 mg/Nm$^3$ | 12 g/h |
| | $CO_2$ | 2.2% v/v | — |
| | $O_2$ | 17.8% v/v | — |

TABLE 5-continued

Gas analysis results of 100% commercial diesel fuel.

| Experiment | Component | Average Concentration | Emission |
|---|---|---|---|
| | TOC ($C_3H_8$) | 22 mg/Nm$^3$ | 1 g/h |
| | $NO_x$ | 295 mg/Nm$^3$ | 14 g/h |

TABLE 6

Particulate matter results of 100% commercial diesel fuel.

| Experiment | Volume Actual [m3/h] | Volume Normal [Nm3/h] | Total particulate matter Concentration [mg/Nm3] | Total particulate matter Emission [g/h] |
|---|---|---|---|---|
| 1 | 63 | 49 | 8.0 | <1 |

TABLE 7

Gas analysis results of blend of commercial diesel with 25 vol % FEE.

| Experiment | Component | Average Concentration | Emission |
|---|---|---|---|
| 2 | CO | 302 mg/Nm$^3$ | 15 g/h |
| | $CO_2$ | 2.2% v/v | — |
| | $O_2$ | 17.7% v/v | — |
| | TOC ($C_3H_8$) | 38 mg/Nm$^3$ | 2 g/h |
| | $NO_x$ | 290 mg/Nm$^3$ | 14 g/h |

TABLE 8

Particulate matter results of blend of commercial diesel with 25 vol % FEE.

| Experiment | Volume Actual [m3/h] | Volume Normal [Nm3/h] | Total particulate matter Concentration [mg/Nm3] | Total particulate matter Emission [g/h] |
|---|---|---|---|---|
| 2 | 63 | 49 | 12.6 | <1 |

TABLE 9

Gas analysis results of blend of commercial diesel with 25 vol % DEMF.

| Experiment | Component | Average Concentration | Emission |
|---|---|---|---|
| 3 | CO | 520 mg/Nm$^3$ | 25 g/h |
| | $CO_2$ | 2.2% v/v | — |
| | $O_2$ | 17.7% v/v | — |
| | TOC ($C_3H_8$) | 96 mg/Nm$^3$ | 5 g/h |

TABLE 9-continued

Gas analysis results of blend of commercial diesel with 25 vol % DEMF.

| Experiment | Component | Average Concentration | Emission |
|---|---|---|---|
| | $NO_x$ | 278 mg/Nm$^3$ | 14 g/h |

TABLE 10

Particulate matter results of blend of commercial diesel with 25 vol % DEMF.

| Experiment | Volume Actual [m3/h] | Volume Normal [Nm3/h] | Total particulate matter Concentration [mg/Nm3] | Total particulate matter Emission [g/h] |
|---|---|---|---|---|
| 3 | 63 | 49 | 23.4 | 1.1 |

Example 6

Emission Engine Testing with Diesel, FME and DMMF

In a manner similar to Example 5, a D9B diesel engine of a Citroen Berlingo test car, comparative testing was performed with normal commercial diesel fuel (experiment 4) and the same commercial diesel to which 25 vol. % FME (experiment 5) or 12.5 vol % DMMF (experiment 6) was added, respectively. FME and DMMF were added as a liquid and do not yield any mixing or flocculation problems at the blend ratio's used. The engine is run stationary with regular diesel initially, after which the fuel supply is switched to the 25 vol % FME-diesel blend and the 12.5 vol % DMMF-diesel blend, respectively.

The results of the measurements are listed in the Tables 11 to 15

TABLE 11

Gas analysis results of 100% commercial diesel fuel.

| Experiment | Component | Average Concentration | Emission |
|---|---|---|---|
| 4 | CO | 205 mg/Nm$^3$ | 7 g/h |
| | $CO_2$ | 2.2% v/v | — |
| | $O_2$ | 17.9% v/v | — |
| | TOC ($C_3H_8$) | 24 mg/Nm$^3$ | 1 g/h |
| | $NO_x$ | 293 mg/Nm$^3$ | 9 g/h |

TABLE 12

Particulate matter results of 100% commercial diesel fuel.

| Experiment | Volume Actual [m3/h] | Volume Normal [Nm3/h] | Total particulate matter Concentration [mg/Nm3] | Total particulate matter Emission [g/h] |
|---|---|---|---|---|
| 4 | 39 | 32 | 6.3 | <1 |

TABLE 13

Gas analysis results of blend of commercial diesel with 25 vol % FME.

| Experiment | Component | Average Concentration | Emission |
|---|---|---|---|
| 5 | CO | 288 mg/Nm³ | 9 g/h |
|  | $CO_2$ | 2.2% v/v | — |
|  | $O_2$ | 17.8% v/v | — |
|  | TOC ($C_3H_8$) | 33 mg/Nm³ | 1 g/h |
|  | $NO_x$ | 308 mg/Nm³ | 9 g/h |

TABLE 14

Particulate matter results of blend of commercial diesel with 25 vol % FME.

| | Volume | | Total particulate matter | |
|---|---|---|---|---|
| Experiment | Actual [m3/h] | Normal [Nm3/h] | Concentration [mg/Nm3] | Emission [g/h] |
| 5 | 36 | 30 | 8.5 | <1 |

TABLE 15

Gas analysis results of blend of commercial diesel with 12.5 vol % DMMF.

| Experiment | Component | Average Concentration | Emission |
|---|---|---|---|
| 6 | CO | 260 mg/Nm³ | 8.5 g/h |
|  | $CO_2$ | 2.2% v/v | — |
|  | $O_2$ | 17.9% v/v | — |
|  | TOC ($C_3H_8$) | 31 mg/Nm³ | 1 g/h |
|  | $NO_x$ | 275 mg/Nm³ | 8.5 g/h |

TABLE 16

Particulate matter results of blend of commercial diesel with 12.5 vol % DMMF.

| | Volume | | Total particulate matter | |
|---|---|---|---|---|
| Experiment | Actual [m3/h] | Normal [Nm3/h] | Concentration [mg/Nm3] | Emission [g/h] |
| 6 | 39 | 32 | 10.6 | <1 |

Example 7

Diesel Fuel Applications

Fuel Solubility

Fuel solubility is a primary concern for diesel fuel applications. Not all highly polar oxygenates have good solubility in the current commercial diesel fuels. Results show that mixtures of 2,5-di(ethoxymethyl)furan and 2-(ethoxymethyl)furan (etherification product, prepared from a mixed C6/C5 starting material) with commercial diesel and mixtures of 5-(ethoxymethyl)-2-methylfuran and 2-methylfuran (hydrogenation product, prepared from a mixed C6/C5 starting material) with commercial diesel are completely miscible in all ratio's. In a comparative set of experiments it was shown that ethoxymethylfurfural (EMF) (prepared from a C6 starting material) is completely miscible in a 5 vol % blend with commercial diesel, but that phase separation occurs with the 25 vol % with the 40 vol % blends of EMF and diesel. Results with an EMF/furfural blend were worse then that with EMF alone.

REFERENCES

DE 635783
DUMESIC, James A, et al. "Phase modifiers promote efficient production of Hydroxymethylfurfural from fructose". Science. 30 Jun. 2006, vol. 312, no. 5782, p. 1933-1937.
WO 2006/063220
Chapter 15 of Advanced Organic Chemistry, by Jerry March, and in particular under reaction 5-4. (3$^{rd}$ ed., © 1985 by John Wiley & Sons, pp. 684-685).
LEWKOWSKI, Jaroslaw. Synthesis, chemistry and applications of 5-hydroxymethylfurfural and its derivatives. Arkivoc. 2001, p. 17-54.
MOREAU, Claude, et al. "Dehydration of fructose and sucrose into 5-hydroxymethylfurfural in the presence of 1-H-3-methyl imidazolium chloride acting both as solvent and catalyst", Journal of Molecular Catalysis A: Chemical 253 (2006) p. 165-169.
EP 0641 854
UOP report OPPORTUNITIES FOR BIORENEWABLES IN OIL REFINERIES FINAL TECHNICAL REPORT, SUBMITTED TO: U.S. DEPARTMENT OF ENERGY (DOE Award Number. DE-FG36-05GO15085))
Adv. Synth. Catal. 2001, 343, 220-225
EP 0 356 703
FR 2 669 634

The invention claimed is:

1. A method for the manufacture of a mixture of a furfural and a 5-alkoxymethylfurfural derivative by reacting a hexose and pentose-containing starting material with an aliphatic C1-C20 alcohol in the presence of an acid catalyst, resulting in a mixture of furfural and a 5-(alkoxymethyl)furfural, followed by the hydrogenation of the mixture of furfural and 5-alkoxymethylfurfural to form a hydrogenation product and the etherification of the hydrogenation product to convert the aldehyde function of both 5-(alkoxymethyl)furfural and furfural into an alkoxymethyl function.

2. The method according to claim 1, wherein the alcohol is a primary, secondary or tertiary.

3. The method according to claim 2, wherein the alcohol is selected from one or more of the group consisting of methanol, ethanol, 1-propanol and 2-propanol.

4. The method according to claim 1, wherein the acid catalyst is selected from the group consisting of homogeneous or heterogeneous acids selected from solid organic acids, inorganic acids, salts, Lewis acids, ion exchange resins, zeolites or mixtures and/or combinations thereof.

5. The method according to claim 1, wherein the acid catalyst is a solid Brønsted acid or a solid Lewis acid.

6. The method according to claim 1, wherein the reaction is performed at a temperature from 50 to 300 degrees Celsius.

7. The method according to claim 1, wherein the hexose is selected from the group consisting of starch, amylose, galactose, cellulose, hemi-cellulose, glucose-containing disaccharides such as sucrose, maltose, cellobiose, lactose, and their oxidized, reduced, etherified, esterified and amidated derivatives.

8. The method according to claim 1, wherein the pentose containing starting material is selected from the group consisting of Arabinose, Ribose, Ribulose, Xylose, Xylulose, Lyxose and their oxidized, reduced, etherified, esterified and amidated derivatives.

9. The method according to claim 1, performed in the presence of a solvent, wherein the solvent or solvents are selected form the group consisting of water, sulfoxides, ketones, ionic liquids, esters, ethers, or the aliphatic C1 to C20 alcohol, and mixtures thereof.

10. The method according to claim 1, wherein the method is performed in a continuous flow process.

11. The method according to claim 10, wherein the continuous flow process is a reactive distillation or a catalytic distillation process.

12. The method according to claim 11, wherein in addition to a heterogeneous acid catalyst, an inorganic or organic acid catalyst is added to the feed of the fixed bed or catalytic distillation continuous flow process.

13. The method according to claim 10, wherein the liquid hourly space velocity ("LHSV") is from 1 to 1000 v/v/hr.

14. A fuel composition comprising an ether as fuel component for engines, optionally blended with one or more of gasoline and gasoline-ethanol blends, kerosene, diesel, biodiesel, Fischer-Tropsch liquids, diesel-biodiesel blends and green diesel and blends of diesel and/or biodiesel with green diesel and other derivatives of furan and tetrahydrofuran,
wherein the ether is produced by reacting a hexose and pentose-containing starting material with an aliphatic C1-C20 alcohol in the presence of an acid catalyst, resulting in a mixture of furfural and a 5-(alkoxymethyl)furfural, followed by the hydrogenation of the mixture of furfural and 5-alkoxymethylfurfural to form a hydrogenation product and the etherification of the hydrogenation product to convert the aldehyde function of both 5-(alkoxymethyl)furfural and furfural into an alkoxymethyl function.

15. The A fuel composition according to claim 14, wherein the ether is selected from the group consisting of furfuryl methyl ether, furfuryl ethyl ether, di(methoxymethyl)furan, di(ethoxymethyl)furan and mixtures thereof.

* * * * *